US009169521B1

(12) United States Patent
Rajagopal et al.

(10) Patent No.: US 9,169,521 B1

(45) Date of Patent: Oct. 27, 2015

(54) POINT-OF-COLLECTION SAMPLE PREPARATION DEVICE AND METHOD

(71) Applicant: The Boeing Company, Chicago, IL (US)

(72) Inventors: Aditya Rajagopal, Irvine, CA (US); Axel Scherer, Barnard, VT (US); Leora Peltz, Seattle, WA (US)

(73) Assignees: The Boeing Company, Chicago, IL (US); California Institute of Technology, Pasadena, CA (US)

(*) Notice: Subject to any disclaimer, the term of this patent is extended or adjusted under 35 U.S.C. 154(b) by 107 days.

(21) Appl. No.: 13/944,621

(22) Filed: Jul. 17, 2013

Related U.S. Application Data

(60) Provisional application No. 61/786,122, filed on Mar. 14, 2013.

(51) Int. Cl.

| | |
|---|---|
| ***C12M 1/00*** | (2006.01) |
| ***C12Q 1/68*** | (2006.01) |
| ***C12P 19/34*** | (2006.01) |
| ***C12M 3/00*** | (2006.01) |
| ***G01N 15/06*** | (2006.01) |
| ***G01N 33/00*** | (2006.01) |
| ***G01N 21/75*** | (2006.01) |
| ***G01N 31/22*** | (2006.01) |
| ***G01N 33/52*** | (2006.01) |
| ***G01N 33/566*** | (2006.01) |

(52) U.S. Cl.
CPC .................................... *C12Q 1/6888* (2013.01)

(58) Field of Classification Search
USPC ................ 435/6.1, 91.2, 283.1, 287.2, 287.8, 435/287.9; 422/68.1, 426, 430; 436/501
See application file for complete search history.

(56) References Cited

U.S. PATENT DOCUMENTS

| | | | | |
|---|---|---|---|---|
| 6,342,347 | B1 * | 1/2002 | Bauer | 435/4 |
| 7,745,207 | B2 * | 6/2010 | Jovanovich et al. | 435/288.5 |
| 2004/0038385 | A1 * | 2/2004 | Langlois et al. | 435/287.1 |
| 2004/0086872 | A1 * | 5/2004 | Childers et al. | 435/6 |
| 2005/0142663 | A1 * | 6/2005 | Parthasarathy et al. | 436/174 |

(Continued)

FOREIGN PATENT DOCUMENTS

WO WO 2012/129157 A2 9/2012

OTHER PUBLICATIONS

U.S. Appl. No. 61/597,520, Feb. 10, 2012, Rajagopal.

(Continued)

*Primary Examiner* — Narayan Bhat
(74) *Attorney, Agent, or Firm* — Moore & Van Allen PLLC

(57) ABSTRACT

A device and method for analyte detection is provided. In an embodiment, the device includes a multi-layer filter configured to receive a fluid-borne sample including at least one analyte in combination with one or more non-analyte components. The multi-layer filter includes a sample preparation layer configured to dissolve upon receiving a portion of the fluid-borne sample to produce a solution including at least a portion of the fluid-borne sample. The device also includes an analysis cartridge for determining a presence and/or a concentration of the analyte in the solution. The device may be configured as a wearable mask or as a part of a ventilation system. In some embodiments, the analyte is detected using a polymerase chain reaction and a detectable marker. The device and method may be used to quickly detect the presence of an analyte in real-time and on-location.

22 Claims, 9 Drawing Sheets

(56) References Cited

U.S. PATENT DOCUMENTS

| | | | | |
|---|---|---|---|---|
| 2007/0122819 | A1* | 5/2007 | Wu et al. | 435/6 |
| 2007/0278097 | A1* | 12/2007 | Bhullar et al. | 204/403.01 |
| 2010/0009456 | A1* | 1/2010 | Prins et al. | 436/164 |
| 2010/0129878 | A1* | 5/2010 | Parthasarathy et al. | 435/91.5 |
| 2010/0136554 | A1* | 6/2010 | Parthasarathy et al. | 435/6 |
| 2012/0264202 | A1 | 10/2012 | Walker et al. | |

OTHER PUBLICATIONS

U.S. Appl. No. 61/597,554, Feb. 10, 2012, Rajagopal.

U.S. Appl. No. 61/466,835, Mar. 23, 2011, Walker.

U.S. Appl. No. 61/477,481, Apr. 20, 2011, Chen.

Industrial Partnerships Office, "Portable Real-time PCR Instrument", downloaded from <https://ipo.llnl.gov/technologies.rss> Apr. 2013, p. 1.

Maltezos et al., "Portable real-time PCR for rapid viral identification" IVD Technology, Nov. 3, 2010, downloaded from <http://www.ivdtechnology.com/article/portable-real-time-pcr-rapid-viral-identification>, pp. 1-8.

Mahjoob et al., "Rapid Microfluidic thermal cycler for polymerase chain reaction nucleic acid amplification", International Journal of Heat and Mass Transfer, 51, Jan. 29, 2008, pp. 2109-2122.

* cited by examiner

POINT-OF-COLLECTION SAMPLE PREPARATION DEVICE AND METHOD

CROSS-REFERENCE TO RELATED APPLICATION

This application claims the benefit of U.S. Patent Application No. 61/786,122, filed Mar. 14, 2013, the contents of which are incorporated herein by reference in their entirety.

TECHNICAL FIELD

This disclosure relates to a sample collection, preparation, and analysis device, more specifically to air sampling devices and methods for point-of-collection sample preparation and analysis.

BACKGROUND

Point-of-collection chemical and biological analyte detection is of ever increasing importance. The form factor for the collection tool may be sized to promote practical use and capable of chemical and biological analyte collection, detection, and analysis. Often biological samples received for point-of-collection analysis will include biological and/or physical contaminants. Traditionally, biological sample preparation entails extensive treatment of biological samples to reduce these contaminants, which is both time-consuming and labor intensive.

DNA and RNA analysis is a tool for various applications, such as detection of disease vectors, identification of samples, and the like. The nature of nucleic acid sequences allows for the detection of biological agents with a high degree of specificity. Given that the concentration of DNA or RNA in biological samples is low, the concentration is often increased, i.e., amplified, to more easily detect the presence and/or concentration of the DNA or RNA. The most common method to amplify nucleic acids is the polymerase chain reaction (PCR). In PCR, a nucleic acid-containing solution is mixed with primer strands that bracket the sequence that will be amplified, free nucleotides, a polymerase enzyme, and buffer solution. The mixture is cycled through a series of temperatures that allow the nucleic acids to separate, anneals the primers to separated strands, and then extends the sequence using the free nucleotides and the polymerase enzyme. As the cycles continue, the total concentration of nucleic acid in the sample doubles, causing the concentration to be exponentially amplified.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

In a first aspect, an analyte detection device is provided. In some embodiments, the device includes a multilayer member configured to receive a fluid-borne sample comprising at least one analyte in combination with one or more non-analyte components, the multilayer member comprising at least: a sample preparation layer configured to dissolve upon receiving at least a portion of the fluid-borne sample to produce a solution comprising at least a portion of the fluid-borne sample; and an analysis cartridge in microfluidic communication with the multilayer member, the analysis cartridge configured to determine a presence and/or a concentration of the analyte in the solution.

In a further embodiment, the sample preparation layer comprises one or more of cell lysis chemistry and a cell lysis device. In some embodiments, the multilayer member further comprises at least one filter element configured to separate at least one analyte from the one or more non-analyte components.

The device may also include a concentrating layer having an affinity technique specific for the at least one analyte. In various embodiments, the affinity technique is based in whole or in part on charge-selectivity, mass-selectivity, antibody-antigen binding, bonding specificity, or a combination thereof.

In some embodiments, the microfluidic communication is between the sample preparation layer and the analysis cartridge. The microfluidic system may include at least one of a capillary tube and a heater in thermal communication with the capillary tube.

In still further embodiments, the device comprises polymerase chain reaction chemistry. In some embodiments, at least a portion of the polymerase chain reaction chemistry is lyophilized in a dissolvable filter. The device may also include a detectable marker specific to one or more of the at least one analyte and an output device configured to provide a visual indicia of the results from the analysis cartridge.

In some embodiments, the device is integrated with a face mask and in other embodiments the device is integrated with a ventilation or air-handling system of a vehicle or building.

In a further aspect, a method for detection of an analyte is provided. In some embodiments, the method includes receiving a fluid-borne sample comprising at least one analyte in combination with one or more non-analyte components; introducing at least a portion of the fluid-borne sample to a sample preparation layer configured to dissolve upon receiving at least a portion of the fluid-borne sample to produce a solution comprising at least a portion of the fluid-borne sample; and determining a presence and/or a concentration of the at least one analyte in the sample.

In some embodiments, the method includes filtering the fluid-borne sample through at least one filter to separate the at least one analyte from the non-analyte component. In further embodiments, the method also includes lysing a cell in the fluid-borne sample to release the at least one analyte in the solution. The lysing may be performed using at least one of chemical lysing, thermal lysing, and mechanical lysing.

In further embodiments, the method includes concentrating the at least one analyte in the analyte-containing solution, wherein the concentrating is based at least in part on an affinity technique. The affinity technique may be based in whole or in part on a charge-selectivity, a mass-selectivity, an antibody-antigen binding, a bonding specificity, or a combination thereof. The method may also include introducing the solution to a microfluidic system and transporting the solution to an analysis cartridge. In some embodiments, the microfluidic system comprises at least one of a capillary tube and a heater in thermal communication with the capillary tube.

In some embodiments, the determination is performed using polymerase chain reaction. In further embodiments, the method includes providing at least a portion of polymerase chain reaction chemistry in a lyophilized form in a dissolvable filter. The method may also include providing a detectable marker specific to the at least one analyte. In embodiments, the detection is performed using an Enzyme-Linked Immunosorbent Assay (ELISA), a quantitative real-time polymerase chain reaction (qPCR), or a DNA-hybridization technique.

In a still further aspect, an analyte detection device is provided. In some embodiments, the device includes a sampling device having one or more sampling ports for receiving a fluid-borne sample, the fluid-borne sample comprising at least one analyte in combination with one or more non-analyte components; a multilayer member in fluidic communication with the one or more sampling ports, the multilayer member comprising at least: a filter layer configured to separate the at least one analyte from the non-analyte components in the fluid-borne sample, a cell lysis layer configured to dissolve upon receiving at least a portion of the fluid-borne sample to produce a solution comprising at least a portion of the fluid-borne sample, and a concentrating layer having an immune affinity column that binds to the at least one analyte, wherein the concentrating layer is configured to dissolve in the solution; and a real-time PCR cartridge in microfluidic communication with the multilayer member, the real-time PCR cartridge configured to determine a presence and/or a concentration of the at least one analyte in the solution.

To the accomplishment of the foregoing and related ends, the one or more embodiments comprise the features hereinafter fully described and particularly pointed out in the claims. The following description and the annexed drawings set forth in detail certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

Figure 1:
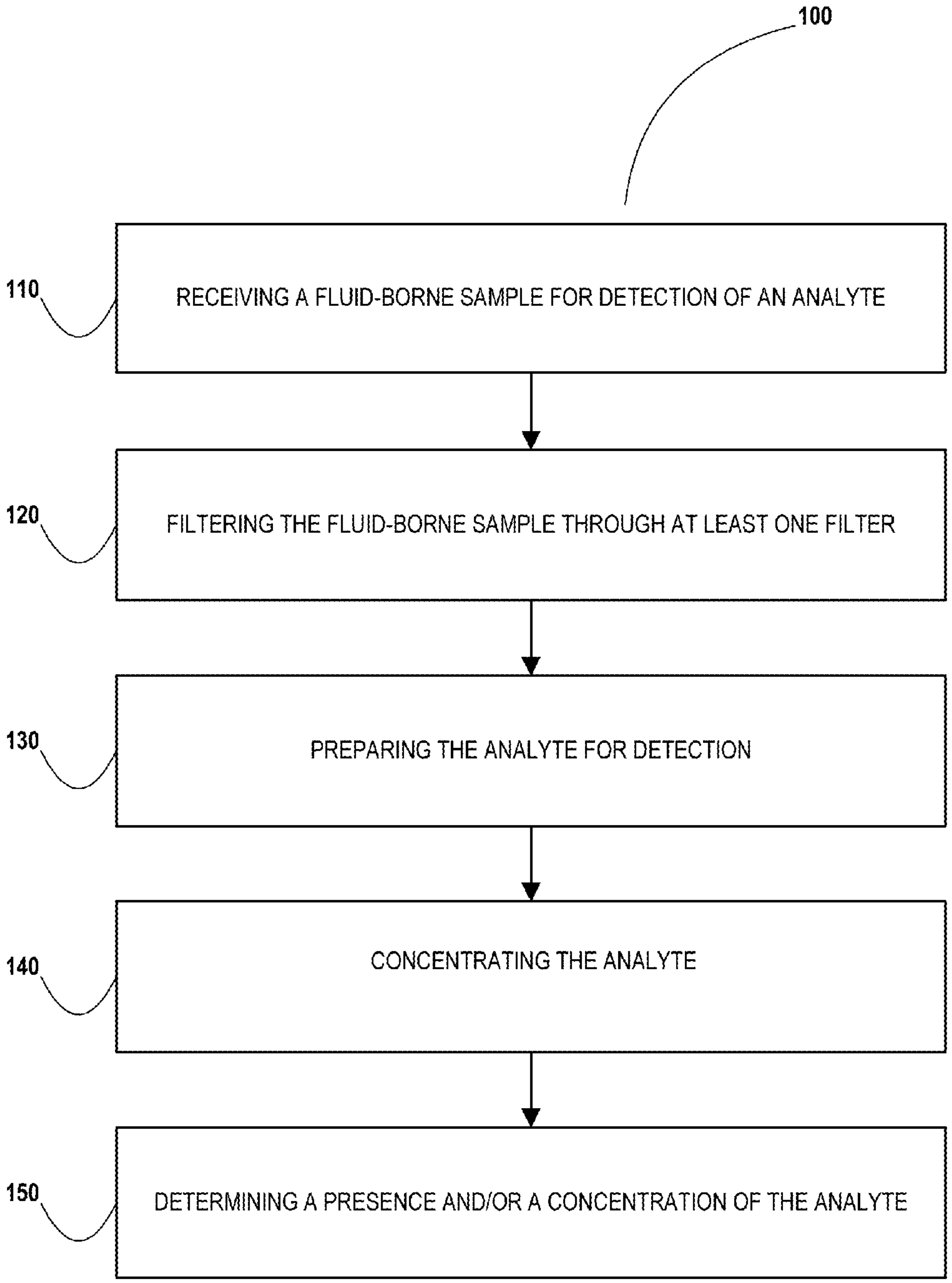
Figure 2A:
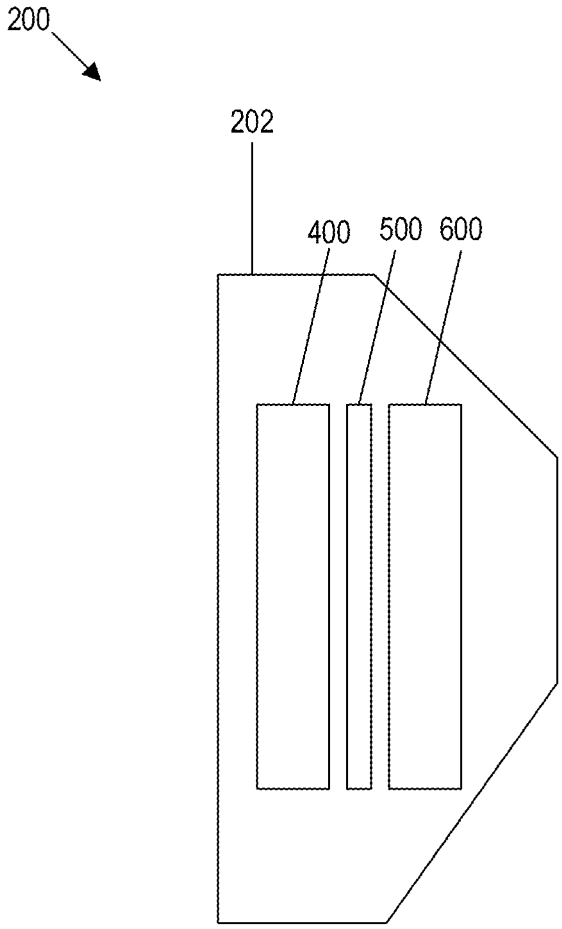
Figure 2B:
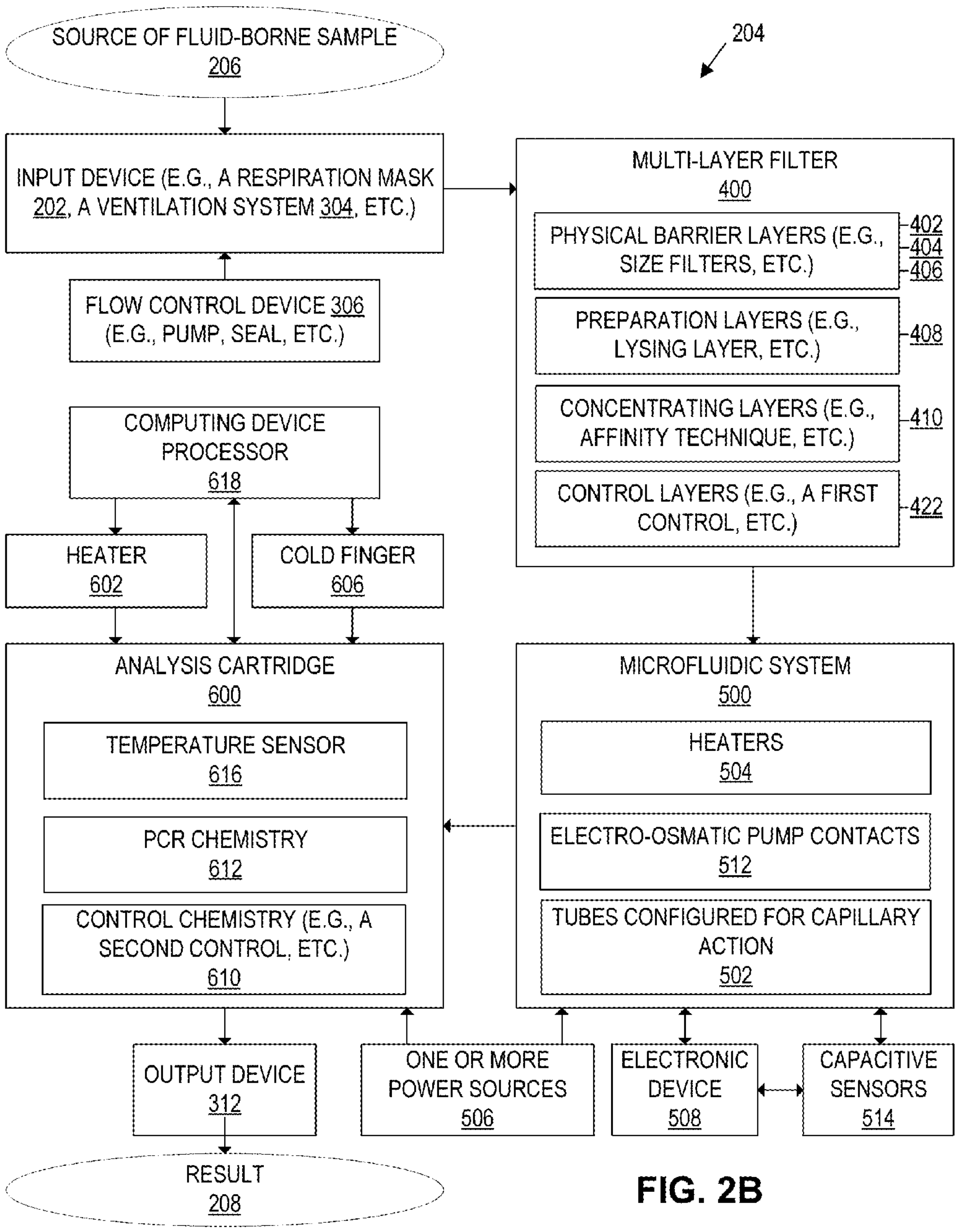
Figure 3:
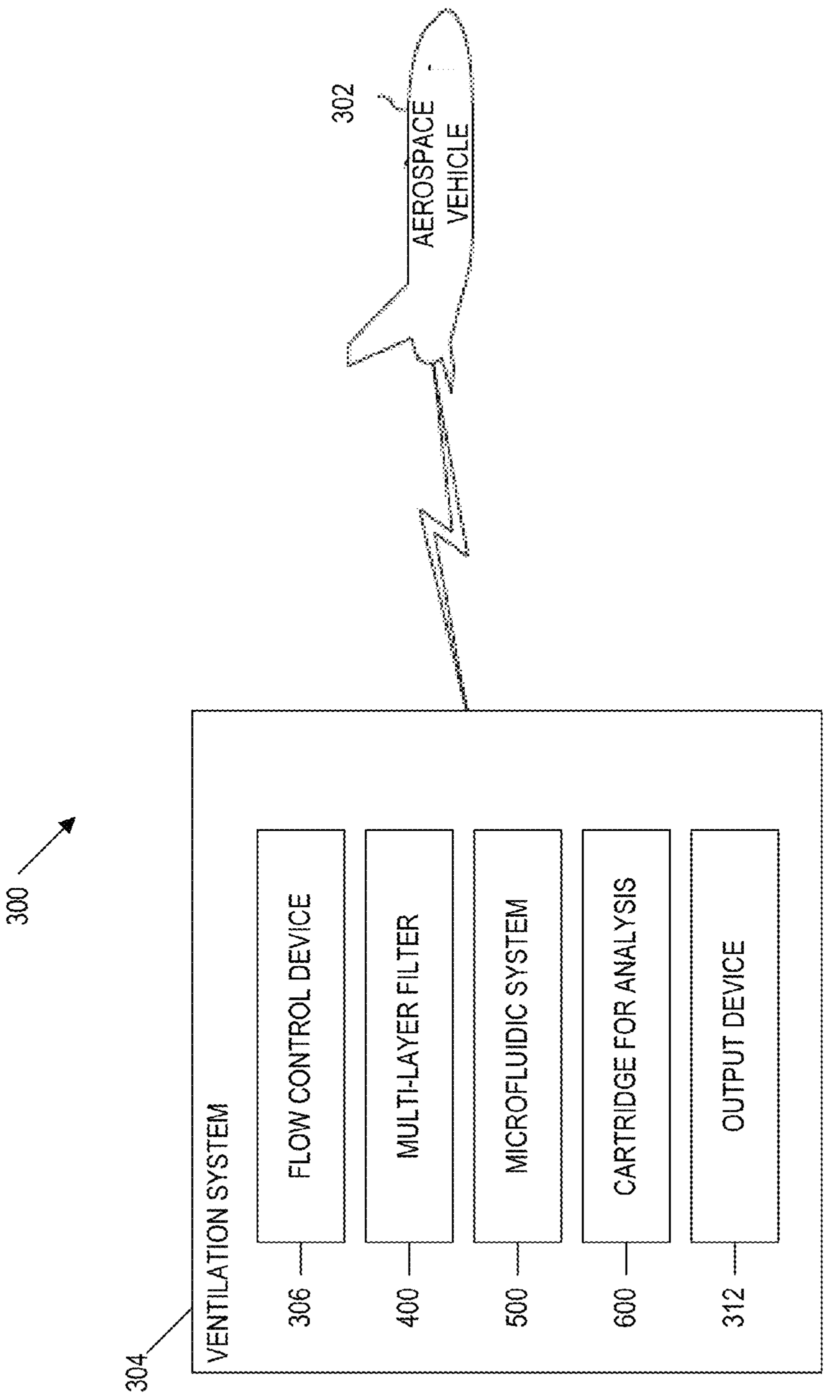
Figure 4A:
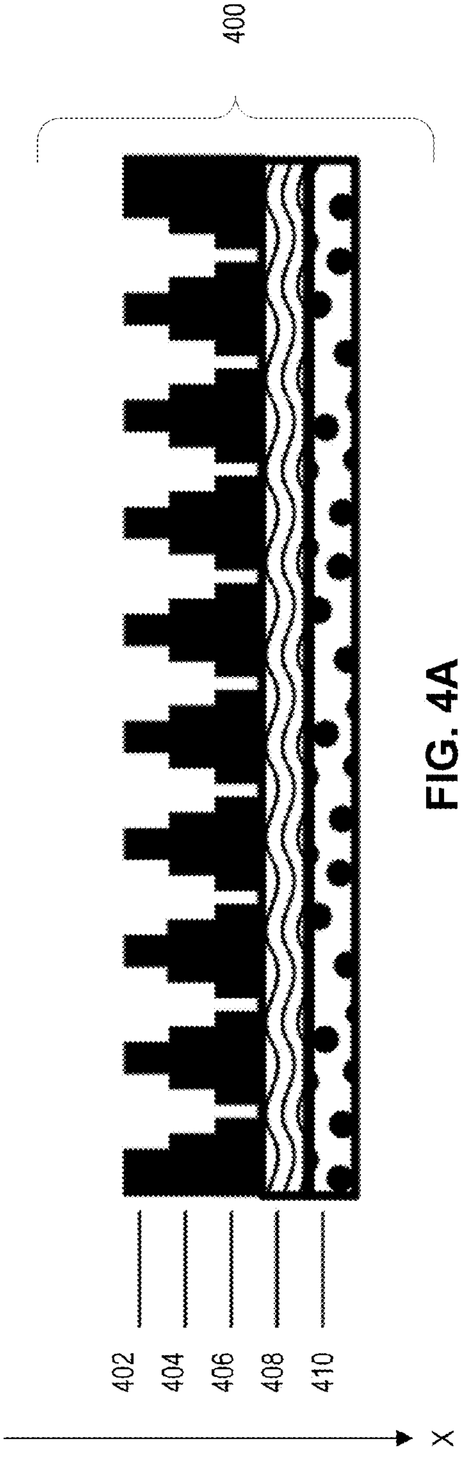
Figure 4B:
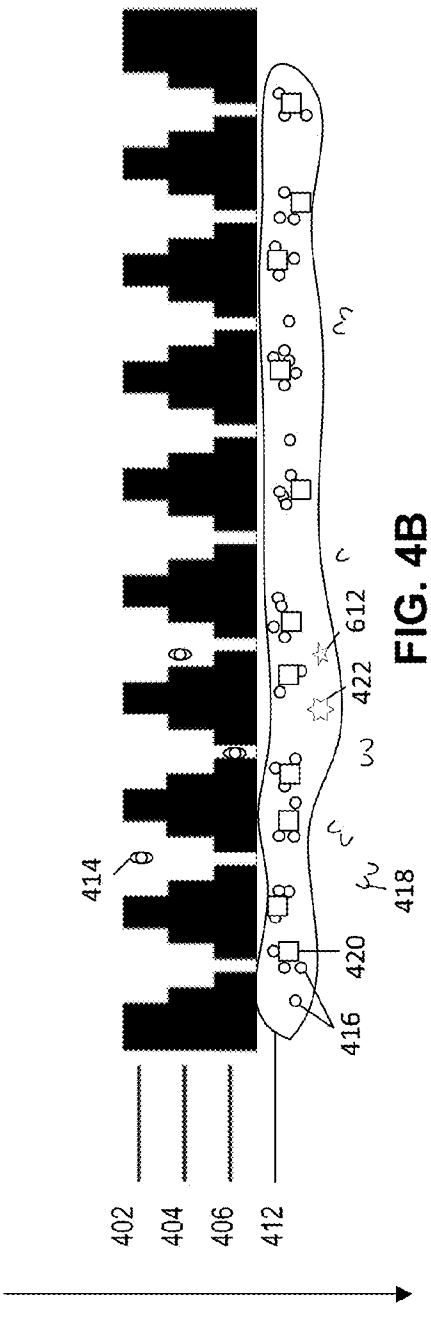
Figure 5:
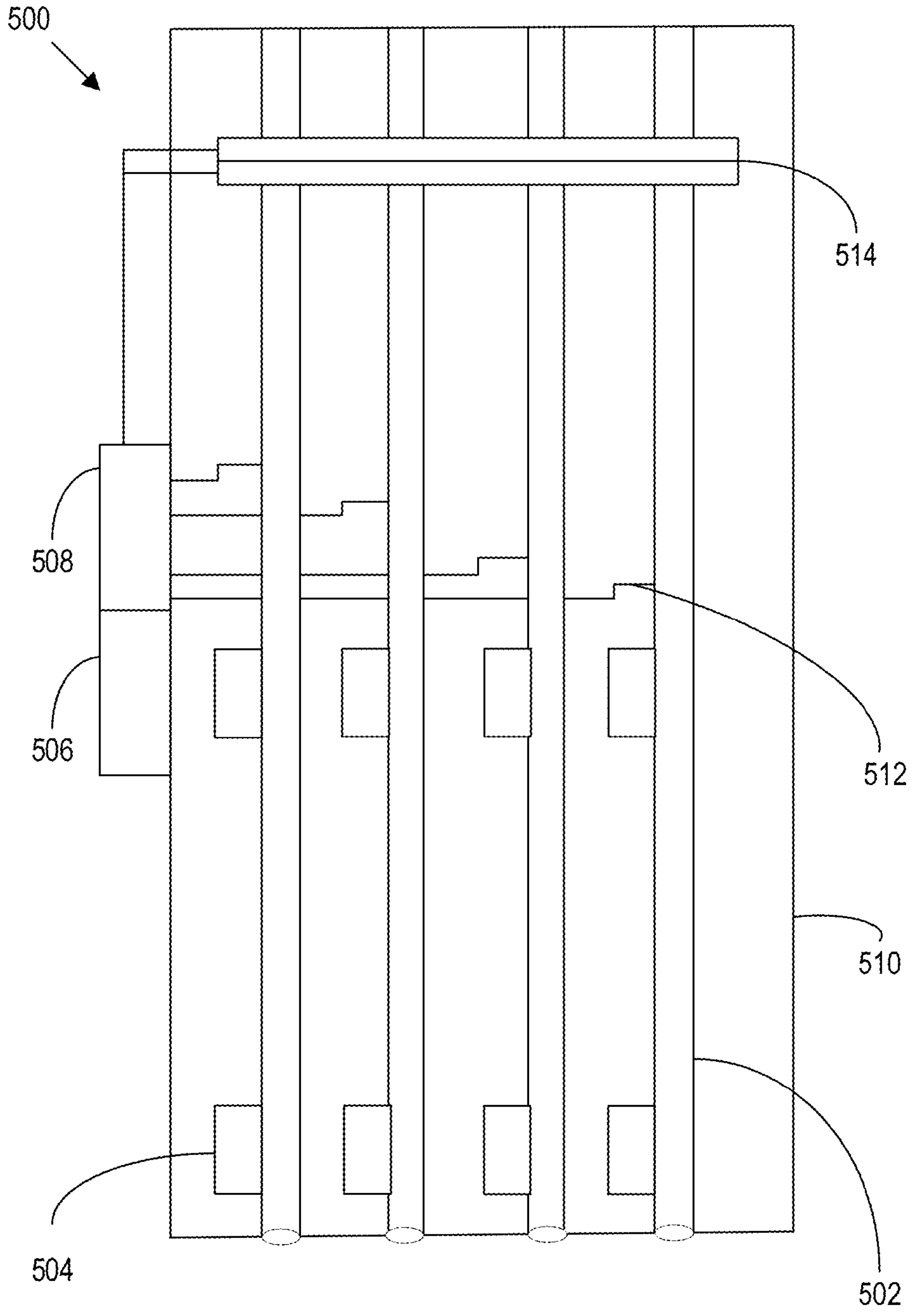
Figure 6:
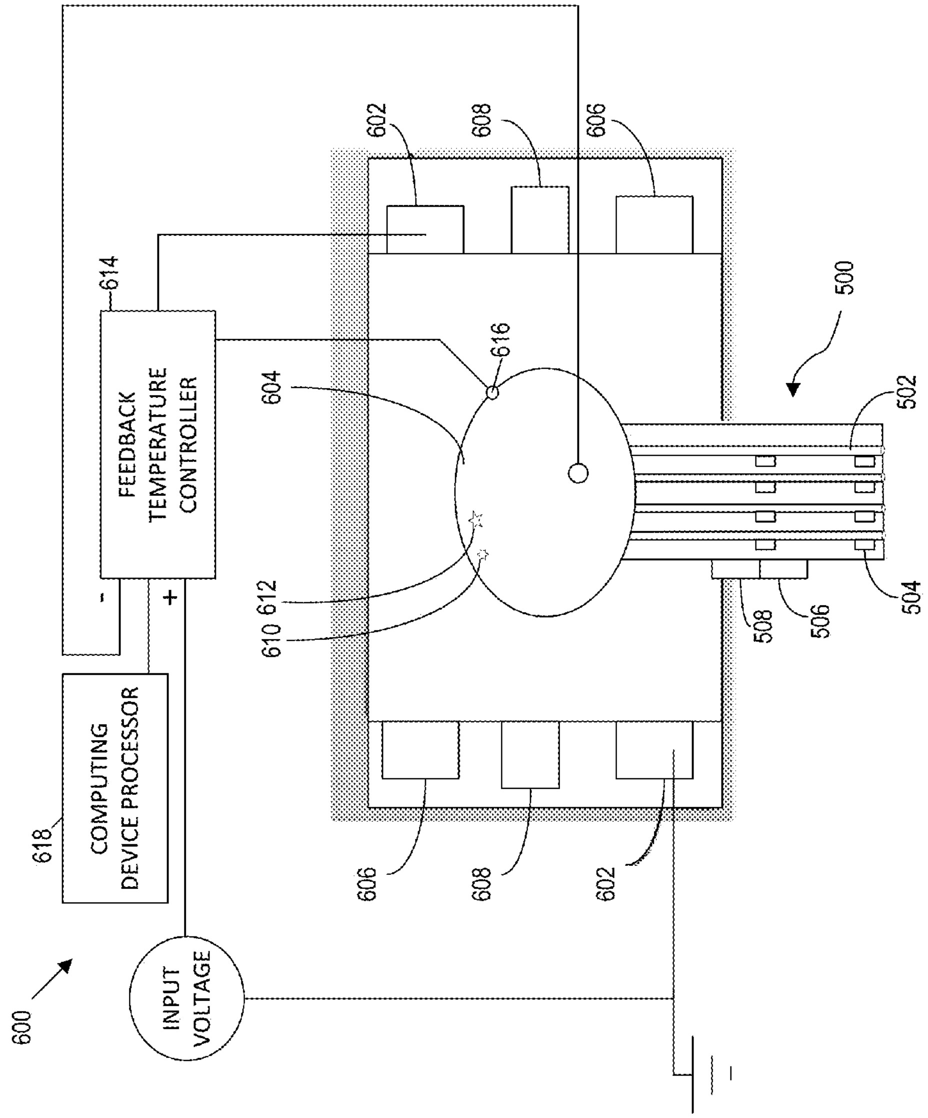
Figure 7:
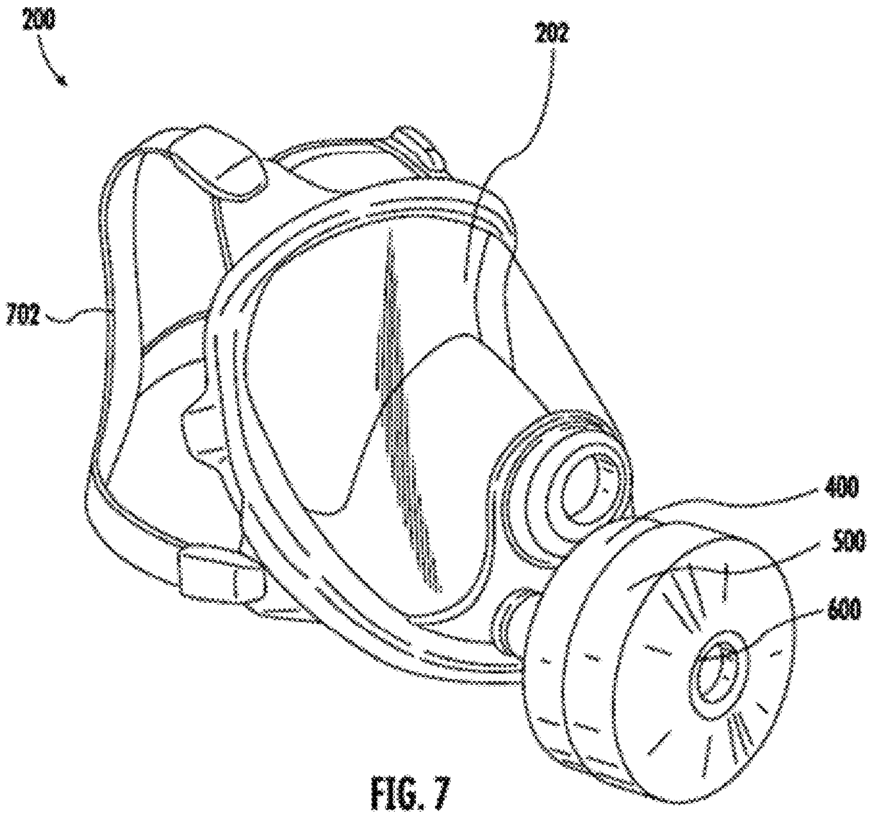
Figure 8:
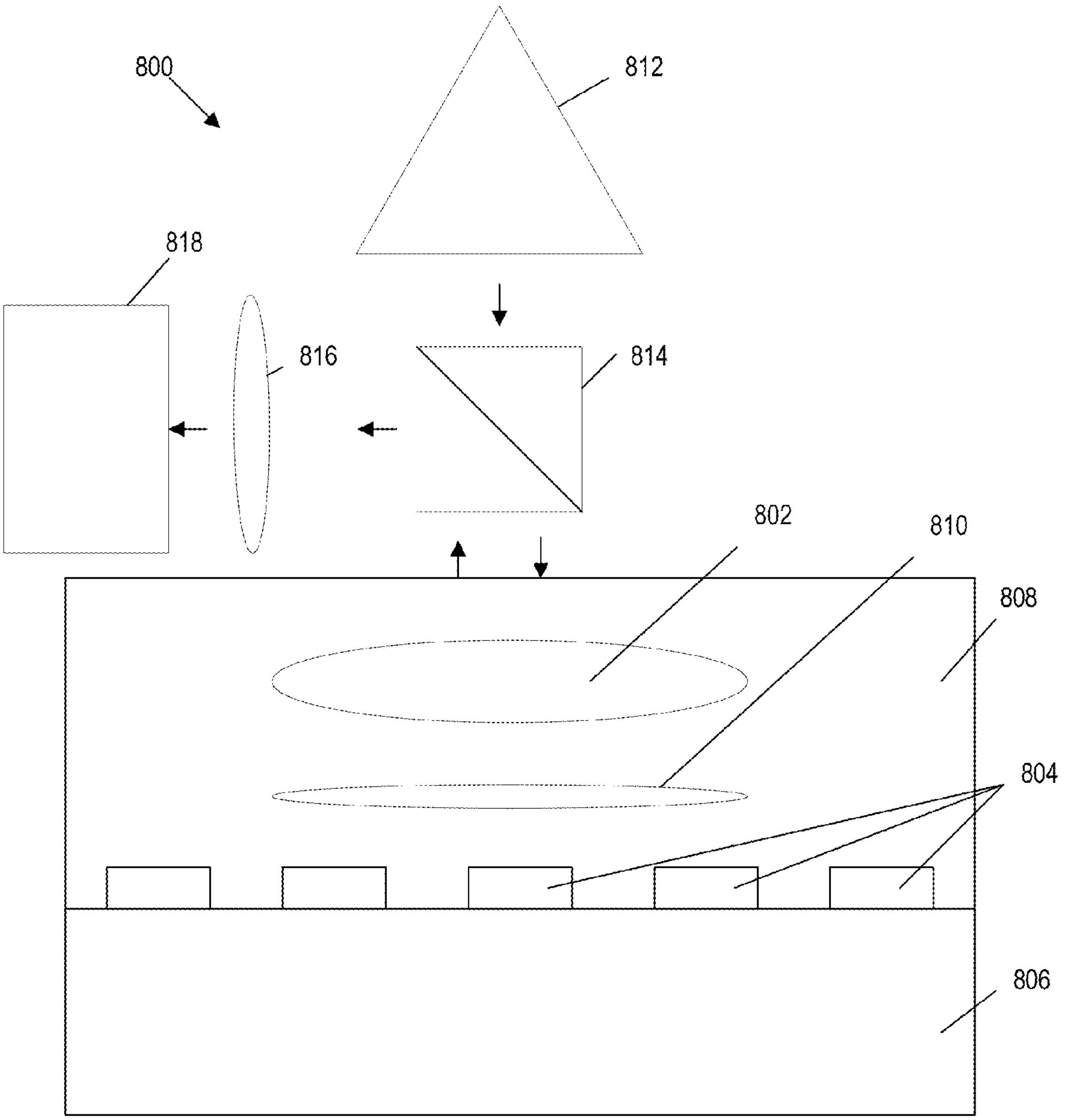

Having thus described embodiments in general terms, reference will now be made to the accompanying drawings, which are not necessarily drawn to scale, and wherein:

FIG. 1 is a process flow chart corresponding to an example method for detection of an analyte in accordance with some implementations of the present disclosure;

FIG. 2A is a schematic representation of an example of a mask-based sample collection, preparation and analysis device in accordance with some implementations of the present disclosure;

FIG. 2B is a functional block diagram corresponding to the functions performed by the elements of the systems and devices disclosed herein in accordance with some implementations of the present disclosure;

FIG. 3 is a schematic representation of a ventilation system comprising a device for analyte detection, in accordance with some implementations of the present disclosure;

FIG. 4A is a schematic representation of an example of a selectively dissolvable multi-layer filter for sample collection in accordance with some implementations of the present disclosure;

FIG. 4B is a schematic representation of an example of a selectively dissolving multi-layer filter for sample collection in accordance with some implementations of the present disclosure;

FIG. 5 is a schematic representation of an example of a microfluidic system in accordance with some implementations of the present disclosure;

FIG. 6 is a schematic representation of a disposable cartridge for performing PCR analysis of a sample collected in accordance with some implementations of the present disclosure;

FIG. 7 is an example of a wearable collection device for detection of an analyte in accordance with some implementations of the present disclosure; and FIG. 8 shows a real-time polymerase chain reaction analysis system comprising a printed circuit board in accordance with some implementations of the present disclosure.

DETAILED DESCRIPTION

Embodiments will now be described more fully hereinafter with reference to the accompanying drawings, in which some, but not all, embodiments are shown. Indeed, many different forms are possible and embodiments should not be construed as limited to the embodiments set forth herein; rather, these embodiments are provided so that this disclosure will satisfy applicable legal requirements. In the following description, for purposes of explanation, numerous specific details are set forth in order to provide a thorough understanding of one or more embodiments. It may be evident, however, that such embodiment(s) may be practiced without these specific details. Like numbers refer to like elements throughout.

The present disclosure describes examples of methods and devices for sample collection, preparation, and analysis, for point-of-collection sample preparation and analysis that may be used for sample analysis for food safety, infectious disease detection, point-of-care disease detection, water quality testing, and/or hospital and school screening. Given the benefits of analyte detection, there is a need for instrumentation contained within a sample collection device that detects analytes while minimizing false-positive or false-negative results. The methods and devices disclosed herein address this need by providing a means for detecting analytes while reducing the noise-to-signal ratio in the analysis. These methods and devices may comprise a means for collection of a fluid-borne sample (e.g., a device having a port to accept a fluid-borne sample), a means for sample preparation (e.g., a selectively dissolvable multi-layer filter), and a means for sample analysis (e.g., a disposable cartridge).

Method of Detecting Analytes

In one implementation, as illustrated in FIG. 1, a method 100 for detection of an analyte is provided. In some embodiments, the method includes receiving a fluid-borne sample for detection of an analyte 110; filtering the fluid-borne sample through at least one filter 120; preparing the analyte for detection 130; concentrating the analyte 140; and determining a presence and/or concentration of the analyte 150. In further embodiments, the device and method may also provide the components used for the analysis such as PCR chemistry, provide one or more controls, and/or provide a microfluidic system for moving the analyte from the sample preparation area of the device to the sample analysis area. It should be understood that, unless otherwise specified, not every step disclosed herein needs to be performed and that the order of the steps may be changed. For example, in some embodiments the analyte is not concentrated using a specific concentration technique or device. Similarly, the analyte may be concentrated from the fluid-borne sample prior to passing through the at least one filter.

Turning now to block 110, in an exemplary embodiment the device receives the fluid-borne sample through a mask configured to rest over a subject's mouth and/or nose. In this embodiment, the subject exhales a fluid-borne sample comprising vapor moisture and an analyte of interest into the mask. In some embodiments, the fluid-borne sample passes through a port and into the device. The subject may be a human or other animal for which the detection of an analyte is of interest. In some embodiments, the mask is configured with an attachment device to securely attach the mask to the subject's face so that the exhalation increases in force. The attachment device may be a strap or other flexible device to hold the mask to the subject's face. In some embodiments, the subject or another user holds the mask up to the subject's face. In still further embodiments, a flow control device such as a gel is placed on surfaces of the mask that contact the subject's face so that a seal is formed between the mask and the subject, thus preventing or reducing contamination from external sources when the subject provides the sample to the device. A diagrammatic representation of the mask is provided in FIG. 2A. A functional block diagram corresponding to the functions performed by the elements of the systems and devices disclosed herein is provided in FIG. 2B.

In a further embodiment, the device receives the fluid-borne sample through a ventilation system. For example, the ventilation system may be an air handling system for an aerospace vehicle, e.g., an airplane, helicopter, or the like. In some embodiments, the ventilation system includes an air handler that forces air through a port and into the filtering, concentrating, preparing, and/or detecting elements of the device. In further embodiments, the ventilation system includes a humidity detection and/or adjustment device, such as a humidifier, to both control the humidity of the air and to provide additional vapor moisture to the fluid-borne sample. Still further, the ventilation system may be on a building or in a vehicle, such as a car or boat. A diagrammatic representation of a ventilation system comprising the disclosed system is provided in FIG. 3.

The device may receive the fluid-borne sample continuously, intermittently, or on demand by the user or subject. In some embodiments, the device receives the fluid-borne sample when a user fits the mask onto the subject. In some embodiments, the device includes a switch to open the port into the device and allow the fluid-borne sample to pass through the port. In a further embodiment, the device receives the fluid-borne sample intermittently when affixed to an aerospace vehicle, a building, or a vehicle. The device may provide a monitoring system to detect the presence of analytes in the atmosphere of the aerospace vehicle, building, or vehicle.

In an exemplary embodiment, a fluid-borne sample may include the analyte of interest as well as other components, such as water vapor, dust, biological contaminants, and/or chemicals. The fluid-borne sample may be a liquid or gaseous sample. In some embodiments, the fluid-borne sample is a defined volume. The device may include a measuring device for determining when a predefined volume of air has passed through the port. In other embodiments, however, the fluid-borne sample is based on a duration that the sample is received. For example, the fluid-borne sample may be the air sample received by the device during a period of time. The period of time may be a period of time defined so that there is a high likelihood, e.g., >90%, that the fluid-borne sample will include the analyte if the analyte is present in the subject. In an embodiment, a practice mode is built into the sample collection regime, such that the subject breathes into the device for a period of time until the subject's respiration is of sufficient strength to cause the analyte to pass through the multi-layer filter. In some embodiments, the practice mode is evaluated, such as by a pressure sensor, to determine if the pressure from the subject's respiration is high enough. If the pressure is not high enough to pass the fluid-borne sample through the multi-layer filter, then the analysis portion is not yet started and/or the user can be instructed to continue or increase respiration force (e.g., to exhale harder and/or longer).

The device and method can be used to detect various types of analytes. In one embodiment, the device and method is used to detect the presence and/or concentration of nucleic acids associated with bacteria or viruses. In this embodiment, the bacteria or virus may be associated with a disease or condition carried by the subject. The device and method may also be used to determine the species of the analyte or subject, for example, by identifying DNA sequences from the subject's DNA that are diagnostic of the species.

In block 120, the device filters the fluid-borne sample through at least one filter. Filtering the fluid-borne sample through at least one filter is performed to separate the analyte from other components present in the fluid-borne sample. For example, the fluid-borne sample from one or more subject's respiratory system, or sample air received from a ventilation system, may include both the analyte of interest and various other components. The other components may be the subject's tissue, other microorganisms, dust, physical debris, and the like. These other components can introduce noise or error into the analysis cartridge by inhibiting the PCR reaction or otherwise interfering with the analysis. The detection of the analyte, i.e., the signal that is being detected, is inhibited when noise is introduced into the analysis. A high noise to signal ratio results in less accurate detection of analytes but by filtering the fluid-borne sample to separate the analyte from other components, the noise to signal ratio can be reduced and accurate detection increased.

In some embodiments, the fluid-borne sample is advanced through the at least one filter based on pressure from the subject's respiratory system. As the subject exhales, the force of the exhale pushes the fluid-borne sample through the filters. As discussed, in some embodiments the device receiving the fluid-borne sample may be configured with a flow control device to increase the pressure from the subject's exhale, e.g., by sealing the contact points between the device and the subject's mouth and/or nose. In a further embodiment, a flow control device is used to advance the fluid-borne sample through the at least one filter. For example, the device may include a flow control device such as a pump or vacuum that causes a positive or negative pressure on one side of the at least one filter in order to advance the fluid-borne sample through the one or more filters. In a further embodiment, a pump is used to move air through the ventilation system and the pump additionally forces the fluid-borne sample through the one or more filters.

In an embodiment, the filters comprise consecutive filter layers through which the fluid-borne sample passes. As the fluid-borne sample passes through each consecutive filter layer, a characteristic of the layer separates the analyte from the other components of the fluid-borne sample. For example, the filter layers may separate the analyte from the other components based on particle size, charge, hydrophobicity, mass, magnetism, or other characteristics.

In one embodiment, a filter based on size or volume (e.g., having a specific pore size) filters out large particles from the fluid-borne sample while allowing the analyte and water vapor to pass through the size filter. An additional layer in the filter may separate the analyte from contaminants based on hydrophobicity. Similarly, an additional filter may separate the analytes from the contaminants based on charge. Antibody filters may be used to eliminate specific contaminants that are known to be present in the fluid-borne sample. For example, antibodies for specific antigens that a subject is known to carry or that may interfere with later analysis may be captured using antibodies on a non-dissolvable filter layer, such that the antigens are filtered out prior to sample lysis. In a still further embodiment, other types of filters are possible. For example, a magnetic filter may be included to eliminate contaminants coming through a ventilation system.

Turning briefly to FIG. 4A, a diagrammatic representation of a multi-layer filter 400 is provided. The multi-layer filter may include multiple layers configured to separate the analyte from contaminants in the fluid-borne sample. In FIG. 4A, five layers: first layer 402, second layer 404, third layer 406, fourth layer 408, and fifth layer 410, are disclosed but any number of layers may be incorporated into the device. The first, second, and third layers 402, 404, and 406 represent layers that filter the fluid-borne sample based on particle size. For example, first layer 402 has a pore size that is greater than second layer 404 and third layer 406. As the fluid-borne sample passes through the multi-layer filter in direction X, large particles are prevented from passing further through the filter as the particles reach a pore size that is smaller than the particle size. Instead of or in addition to filtering the fluid-borne sample based on size, the layers may filter the fluid-borne sample based on charge, hydrophobic nature, or other characteristics. In an embodiment, fourth layer 408 is a dissolvable layer that includes a cell lysis compound that is activated when the layer dissolves. In some embodiments, the fourth layer 408 dissolves in part because of the water vapor in the fluid-borne sample. Fifth layer 410 may be a concentrating layer comprising antibodies or other compounds that have affinity for the analyte of interest. As the fluid-borne sample passes through the multi-layer filter 400, contaminants are filtered out by first, second, and third layers 402, 404, and 406, the cell is lysed after passing through fourth layer 408, and the analyte is concentrated in fifth layer 410.

In block 130, the device prepares the analyte for detection. In some embodiments, preparing the analyte for detection comprises lysing cells to release nucleic acids from the cells. Lysing of cells may be accomplished by various low power, portable cell lysis techniques including, but not limited to, chemical lysis, thermal lysis, mechanical lysis, and any combination thereof.

In some embodiments, lysing cells is performed by including a lyophilized lysis solution in a dissolvable filter layer. As used herein, a dissolvable filter layer may be referred to as a membrane. The lysis solution and, in some embodiments, a salt solution are lyophilized in a filter layer. The lysis solution filter layer may comprise a material that is selectively solvent in a fluid such as water, phosphate buffer solution (PBS), or bovine serum albumin (BSA). The moisture in the fluid-borne sample dissolves the material and reconstitutes the active chemistry of the lysis solution.

In further embodiments, cells are lysed by thermal and/or mechanical means, such as a heating element that lyses cells or a mechanical device that grinds tissue or cells. Other methods of lysing cells, such as via sonication, may also be used.

In block 140, the device concentrates the analyte from the fluid-borne sample. In an embodiment, a concentrating layer is provided in the filter layers. For example, a layer may be positioned so that the fluid-borne sample passes through the concentrating layer after the cells are lysed. In an embodiment, the concentrating layer is functionalized with antibodies, hydrocarbons, and other chemistries to attach to at least a portion of the analyte of interest. By attaching to the analyte of interest, the concentrating layer traps the analyte as it passes through the filter. In some embodiments, the concentrating layer is selectively dissolvable in the solution, such as being comprised of cellulose. As will be discussed later, in some embodiments after the concentrating layer dissolves, the solution containing the concentrated analyte is moved to an analysis cartridge, such as via a microfluidic system.

FIG. 4B depicts the embodiment where the preparation layer and the concentrating layer have dissolved from the moisture in the fluid-borne sample. In this example, a cell 414 or microorganism is lysed by the lysis chemicals in the solution 412 and the analyte 416, e.g., a nucleic acid, is released into the solution 412. In some embodiments, the analyte 416 is attracted to an object 420 having affinity with the analyte 416, such as an antibody. In an embodiment, the fifth layer 410 dissolves after the fourth layer 408 because of position, i.e., the fluid reaches the concentrating layer after it reaches the preparation layer, and/or because of the composition of the concentrating layer compared to the preparation layer. Non-analyte components 418, such as proteins or other components of the cell, that are released during lysis may be washed away while the analyte concentrates in the concentrating layer. This further reduces the noise to signal ratio in the analyte-containing solution. When the concentrating layer dissolves, the analyte-containing solution contains the analyte, the compound having affinity for the analyte, and in some embodiments PCR chemistry and controls.

In an embodiment shown in block 150, the device and method provide the components for a PCR analysis, such as real-time or quantitative PCR (qPCR), in order to determine a presence and/or concentration of the analyte. Quantitative PCR allows the user to monitor the progress of PCR as it occurs and provides information on the concentration of DNA in a sample. Other types of PCR analysis may also be performed to detect the presence and/or concentration of the analyte.

In one embodiment, the components in the form of PCR chemistry 612 are provided as part of a dissolvable filter or membrane. In an embodiment, the water vapor in the subject's breath or as part of the ventilation system causes the dissolvable filter to dissolve and rehydrate lyophilized components for the PCR analysis. For example, enzymes, nucleotides, a buffer solution, and one or more primer pairs are included as lyophilized components in the dissolvable filter. The dissolvable filter may include lyophilized magnesium, calcium, sodium, chlorine ions, Taq polymerase, and/or reverse transcriptase. The dissolvable filter may be a part of one or more of the filters discussed previously, such as the lysis solution filter layer or the concentrating layer, or the components may be in their own filter layer. Furthermore, separate components of the PCR chemistry 612 may be in separate filters, or multiple filters. Additionally, some or all of the PCR chemistry 612 may be in lyophilized form or other stable form in the analysis cartridge and/or the tubes of the microfluidic system, such that when the analyte-containing solution passes through the microfluidic system and enters the analysis chamber the PCR chemistry is activated.

In an embodiment, the enzyme is a heat-stable polymerase such as Taq polymerase. In a further embodiment, the components also include reverse transcriptase as an enzyme. In an embodiment, the nucleotides (dNTPs) include dATP, dCTP, dGTP, and dTTP. The buffer solution is designed to maintain the nucleic acids during transport to the cartridge and during the analysis in the cartridge. The buffer solution may include magnesium chloride.

In a still further embodiment, a detectable marker, such as nanosized gold particles, fluorophores, intercalating dyes, FRET probes, antibodies, aptamers, biotinylated and/or streptavidin systems, or the like are included in the device. For example, SYBR Green, SYBR Gold, molecular beacons, and/or scorpion probes may be included as fluorophores. In an embodiment, the detectable marker is specific to the analyte of interest. In an embodiment, the detectable marker is present outside of the analysis cartridge. For example, the detectable marker may be present in a dissolvable filter layer. In another embodiment, the detectable marker is present in the analysis cartridge. For example, the detectable marker may be in lyophilized form in the analysis cartridge and may be activated when the analyte-containing solution enters the analysis cartridge. The detectable maker is configured to indicate to the user when the analyte is detected based on the analysis of the analysis cartridge. For example, the detectable marker may cause a visible or detectable optical signal, such as a fluorescence signal, to be emitted when the analyte is amplified. In another example, a colorimetric marker is used to indicate presence or absence of the analyte.

In some embodiments, the primers are selected based on the analyte of interest. For example, a primer pair specific to a disease that is being evaluated may be included in the dissolvable filter. In some embodiments, multiple primers are included to evaluate different types of diseases or to confirm via multiple primer pairs that a specific disease is present. For example, three primer pairs directed to different regions of DNA from *Mycobacterium tuberculosis*, the mycobacteria that causes tuberculosis, may be included in the dissolvable filter. Any analyte that is detectable based on specific primer pairs can be detected using the device and method disclosed herein. One skilled in the art would understand that other primer pairs, such as primer pairs specific to Avian influenza (e.g., H5N1), HIV/AIDS, Hepatitis B, Herpes simplex I and II, Influenza A, Influenza B, Human rhinovirus, adenovirus, PIV1, PIV2, PIV3, PIV4, mononucleosis, tuberculosis, malaria, ebola, dengue virus, yellow fever, and/or cytomegalovirus, etc., may be included as part of the device.

In some embodiments, one or more controls are provided. In some embodiments, two controls are used to determine whether there was a failure in analyte procurement, e.g., the analyte was not present in the fluid-borne sample, or in analyte detection, e.g., a failure of the PCR to amplify the analyte.

In one embodiment, a first control 422 is included to determine if a portion of the fluid-borne sample entered the analysis cartridge. In an embodiment, the first control includes a sample and a primer pair specific to the sample. In some embodiments, the first control 422 is positioned outside of the analysis cartridge, for example, in lyophilized form in the dissolvable filter along with the other components for the PCR analysis. In a further embodiment, the first control 422 includes a detectable marker, such as a fluorophore, that is distinct from the detectable marker for the analyte or analytes of interest and any other control. The fluorophore specific to the first control may be of a different wavelength than the other detectable markers. The first control 422 is designed so that the detection of its presence in the analysis cartridge indicates that a solution from outside of the analysis cartridge entered into the cartridge. In this manner, the user of the device can confirm that a biological sample received from the environment has entered the analysis cartridge.

In some embodiments, a second control 610 is included in the analysis cartridge to determine if the analysis completed successfully. For example, the second control 610 may be used to determine whether the PCR analysis in the cartridge amplified a sample known to be present in the cartridge. In this embodiment, the second control 610 includes a sample and a primer pair specific to the sample. In an embodiment, the sample and the primer pair are different from any other sample and primer pair being evaluated by the device. The second control 610 may also include a detectable marker that is specific to the sample and different from any other detectable marker used by the device. For example, the detectable marker for the second control may be a fluorophore that fluoresces at a different wavelength from any other detectable marker in use. The second control 610 is designed so that the detection of its presence in the analysis cartridge indicates that the analysis successfully amplified at least one product present in the analysis cartridge.

In a further embodiment, the analyte is transferred from the sample preparation area of the device to the analysis area of the device. In one embodiment, the analyte is transferred via a microfluidics system configured to transfer small quantities of fluid from the sample preparation area to the analysis cartridge. In some embodiments, the microfluidic system comprises one or more tubes having a small-diameter lumen that transports the fluid via capillary action. In further embodiments, the microfluidic system includes heating devices that transports the fluid by selectively heating portions of the device and advancing the fluid based on thermal dynamics. In a still further embodiment, both capillary action and selective heating may be used. Other devices for transporting the fluid may be used, such as one or more of wicking material, suction devices, fans, or passive pressure based on respiration or ventilation.

In a further embodiment, the method includes outputting the results of the analysis. For example, an output device such as a window or display may be provided that displays the colorimetric readout from the one or more detectable markers. A fluorogenic marker may be detected based on the presence of fluorescence. In some embodiments, a light emitting diode or other device for causing and/or reading fluorescence from the fluorogenic markers may be included in the device.

The method for detecting an analyte may be implemented via one or more computing device processors, such as a computing device processor that operates the analysis cartridge. For example, a microprocessor may control the thermocycling of the analysis cartridge. The method may be implemented in a mask-based device or in a ventilation-based device, as will be discussed further with respect to FIGS. 2A and 3.

Mask-Based Device for Detecting Analytes

In some implementations, a fluid-borne sample may be collected from a subject (e.g., a person) through respiration using a collection device, such as one example shown in FIG. 2A. The wearable collection device 200 for sample preparation disclosed in FIG. 2A comprises: (a) a respiration mask 202 designed to fit over a subject mouth and/or nose, (b) a selectively dissolvable, multi-layer filter 400, (c) a microfluidic system 500, and (d) a cartridge 600 for sample analysis. In one aspect, one or more layers capable of separating the biological analyte of interest from contaminants is provided. The multi-layer filter may also include a filter for preparing the sample by lysing cells and a filter for concentrating the analyte of interest. In some embodiments, the cartridge for sample analysis comprises an output device for reporting or indicating the results of the analysis to an observer and/or the subject.

The device is not intended to be used inside the respiratory system of the subject. Instead, the device receives respiration from the subject and an associated fluid-borne sample contacts the multi-layer filter. In this embodiment, analysis of the fluid-borne sample may be considered to be in situ and/or ex vivo because the fluid-borne sample is analyzed in the device that receives the sample. In other embodiments, however, all or part of the steps of the analysis may be performed in a separate device or machine. For example, the multi-layer filter and the cartridge may be removable and/or replaceable. Furthermore, the analysis and/or the identification of the results may be performed in or by external devices. In a further embodiment, the device may perform the analysis and the cartridge may be removable for transport to another analysis or diagnostic device, for example, to confirm the analysis and/or perform additional analyses.

In use, natural pressure gradients (or force) from the subject's respiration urge biologically-associated vapor from the subject's respiratory system into the respiration mask 202 and into contact with the multi-layer filter 400. In an embodiment, the contacted multi-layer filter 400 provides a sample that enters the cartridge 600 (e.g., via the microfluidic system 500). In various embodiments, the cartridge for sample analysis is a real-time quantifying/detecting device (e.g., Enzyme-Linked Immunosorbent Assay (ELISA), a quantitative real-time polymerase chain reaction (qPCR), or a DNA-hybridization technique) or a PCR reactor chamber that performs polymerase chain reaction (PCR)-type amplification of deoxyribonucleic acid (DNA).

The respiration mask 202 is configured to be placed over a subject's mouth and/or nose and receive a fluid-borne sample from the subject's respiration. The respiration mask 202 may include one or more features to enhance the likelihood that the fluid-borne sample will be received and to reduce the chance of contamination. For example, the respiration mask 202 may include a face-conforming seal, e.g., of silicone or polyurethane rubber, gel, and/or an adhesive that reduces loss of respiration and/or increases the effective pressure of the subject's respiration through the mask and/or decreases the chances of contamination from the outside environment. The respiration mask 202 may also include a pressure sensor to determine when the respiration is of sufficient force to cause a fluid-borne sample to pass through the multi-layer filter. In a still further embodiment, the respiration mask 202 includes a one-way filter and/or check-valve (not shown) that allows the fluid-borne sample to pass into the multi-layer filter, but does not allow liquids or gases to pass from the multi-layer filter back into the subject's respiratory system, such as when the subject inhales. The respiration mask 202 may include an intake valve (not shown) that allows outside air to be inhaled by the subject, but prevents/reduces exhaled air from escaping the mask. In an exemplary embodiment, the fluid-borne sample may be that of one or more humans but it should be understood that the present devices or the present methods may be configured for testing respiration of one or more non-human (domesticated and/or livestock) animals or birds as well.

The multi-layer filter 400 may be a physical "egg-sort" filter (or membrane) used to sift a fluid-borne sample and to select an analyte or a target based on one or more parameters, including, but not limited to hydrophobicity, charge, mass, volume, antibody-antigen binding, a bonding specificity, or a combination thereof. For example, a multi-tiered physical barrier as shown in FIG. 4A as physical barrier layers 402, 404, and 406 can be used to physically separate cells from a collected sample media. For example, this configuration can be used to select tuberculosis spores in a respiratory mist sample. Further, the filter sections can be used to select for charge and/or hydrophobicity by selection and preparation of the filter material. For example, a filter section made of silicon dioxide can be used to select for hydrophobic samples. In one embodiment, the physical dimensions of the barriers range in size from 1 mm to 100 nm.

In an embodiment, the final two layers of the multi-layer filter 400 for sample collection are comprised of a material selectively solvent in a fluid (e.g., water, phosphate buffer solution (PBS), or bovine serum albumin (BSA)). In one implementation, the fourth layer 408 may include a cell lysis buffer and salt solutions, thus providing an active chemistry layer that may be reconstituted by moisture contained in the collected fluid-borne sample, and would act on the sample while it is moving through the multi-layer filter 400 (or membrane).

In some implementations the multi-layer filter 400 or membrane may use one or more immunoaffinity purification techniques. In an embodiment, a filter layer comprises a baffle system coated with antibodies. In other implementations, the sections can be coated with an antibody for enzymatic capture of a target, such as bacteria or virus particles. After the fluid-borne sample moves through the aforementioned layers of the multi-layer filter 400, the analyte(s) or target(s) of interest are captured in the fifth layer 410. This layer may be comprised of a material that facilitates dissolution (e.g., cellulose, polyvinyl alcohol, poly vinyl pyrrolidone, poly lactic acid and may be surface modified for nucleic acid capture. These surfaces may also be functionalized by known means (e.g., antibodies, hydrocarbons, and/or other suitable chemistries). In one aspect, the fifth layer 410 can be configured such that it can be physically removed and dissolved in a PCR buffer solution and/or for further sample analysis.

In some embodiments, the microfluidic system 500 transfers the analyte of interest, along with any other solution that is used for the analysis into the cartridge for sample analysis. An example of the microfluidic system 500 is shown in FIG. 5. In some embodiments, capillary action caused by a tube 502 having a small-diameter lumen formed in a substrate and/or heating devices are used to move the fluid from one location to another location. The temperature range for heating the tube may be determined by one skilled in the art based on the diameter of the tube, the analyte concentration of the solution, and/or materials used in construction of the tube. In one aspect, the temperature range may be between 0° C. and 100° C. In a further aspect, the temperature range may be between room temperature and 60° C. The substrate may be a rigid or flexible substrate, such as FR4 substrate used in constructing printed circuit boards. Movement of fluid in the tubes 502 can be configured to be omni-directional or bi-directional. For example, the fluid from the final dissolvable filter may pass into a capillary tube and, via both capillary action and selective heating, be moved from where the fluid is collected to the analysis cartridge. The selective heating may be performed by heaters 504 positioned in thermal communication with the tubes 502 and configured to urge fluid through the tubes 502. In another embodiment, the transportation of the fluid may be performed via electronic devices 508 that control electro-osmatic pump contacts 512 which are in communication with the tubes 502. Electro-osmatic pump contacts 512 generate flow or pressure by use of an electric field. The electro-osmatic pump contacts 512 may be either shorted directly and grounded to prevent significant electroplating etch or separated by dissoluble polymer. The heaters 504 and/or electronic devices 508 may be powered by power sources 506, such as batteries, alternating current, direct current, or other types of portable and non-portable power sources. In some embodiments, capacitive sensors 514 coupled to the electronic device 508 provide for monitoring of the flow within the tube 502. As used herein, the terms "fluid" or "fluidic" and their grammatical equivalents refer to liquids and/or gases. In some embodiments (not shown), the microfluidic system includes a one-way filter that allows solution to pass into the analysis cartridge but not be removed from the cartridge.

In an embodiment, the cartridge for sample analysis is a PCR reactor chamber including a sealed chamber with a cartridge 600 having one or more heaters 602 integrated with the cartridge 600. The chamber allows for the inclusion of a fluid-borne sample ranging from about 0.01 mL to about 3.0 mL. This volume is thermally cycled by heating from the heater(s) 602. In an embodiment, the heaters 602 are integrated into the cartridge 600. In an embodiment, the temperature range for PCR amplification and detection will range from about 37° C. to about 105° C. The temperature range may be optimized for the specific PCR conditions, for example based on the primers. In an embodiment, the heater is powered by a power source 608, such as a 2 watt battery integrated into the device body. Turning briefly to FIG. 6, an example of the cartridge 600 for sample analysis is provided. The cartridge 600 includes one or more heaters 602 for thermocycling the sample and a well 604 for receiving the analyte-containing solution. FIG. 6 also includes an example of the microfluidic system 500 of FIG. 5. It should be understood that a single power source may power the heaters and/or cold-finger air sources of both the cartridge and the microfluidic system. Wiring (not shown) is provided to connect any one or more of the heaters, fans, and computing devices, in parallel or in series, to one or more of the power sources.

A cold-finger air source 606 using external air flow may cool the sample volume during the PCR process. In some embodiments, a fan is used to pass air over a device configured to lower the temperature of the solution in the cartridge. In an embodiment, the air may be ambient air, which is at a lower temperature than the chamber, and or the air can be cooled below ambient. As the ambient air contacts the chamber or an element of the device in thermal communication with the chamber, the temperature of the chamber is reduced. For example, heating can be terminated and ambient air allowed to dissipate heat from the chamber, and the cycle can be repeated. In an embodiment, the fan is coupled with a thermocouple to form a feedback temperature controller 614. The fan may be powered by the power source 608 integrated into the cartridge. In another example, the air may be configured to contact a highly-thermally conductive metal, such as copper, brass, copper, aluminum, or alloys thereof, etc., which contacts or integrates with the analysis cartridge.

The temperature in the PCR reactor chamber may be monitored with a sensor 616. The sensor 616 may be, for example, a resistance temperature detector (RTD) or a thermocouple. Further, in some implementations the sensor 616 may be built-in. The PCR reactor chamber analysis and detection may be done either in the collection means or external to the collection means. Thus, in some embodiments the cartridge is removable. The cartridge may be removed prior to the PCR analysis and in this embodiment, the thermocycler and detection devices may be provided external to the device. In another embodiment, the PCR reaction is completed in the cartridge for sample analysis but the detection of the analyte is performed external to the device. In a still further embodiment, the reaction and an initial detection are performed in the device, but a more comprehensive detection may be performed external to the device. For example, the device may detect the presence of the analyte but not detect the concentration of the analyte. In an embodiment, the temperature range for PCR amplification and detection will range from about 37° C. to about 105° C. As one skilled in the art would know, the temperature range may be optimized for the specific PCR conditions, including the primers.

In further embodiments, the device includes an output device for reporting the results of the analysis. In an embodiment, the output device may present results of the analysis to a user. For example, the output device can be a window, a display screen, an audio signal, a mechanical indicator, and/or a vibratory signal. For example, a window may be present that displays the results of the colorimetric analysis or that displays fluorescence from a fluorometric marker. In a further embodiment, the output device is a display, such as an electronic display or a colorimetric display. In an embodiment, the output device includes a fluorescence detector and/or light emitting device to cause fluorescence if the analyte is present.

The temperature control and detection may be performed in association with a computing device processor 618, which is operably linked to the feedback temperature controller 614 and the output device 312. As discussed, a computing device processor may be a microprocessor, chip, or other computing device. The computing device processor 618 may be powered by the same or different power sources 506 as the microfluidic system 500.

FIG. 2B provides a functional block diagram 204 corresponding to the functions performed by the elements of the systems and devices disclosed herein in accordance with some implementations of the present disclosure. As shown in FIG. 2B, a fluid-borne sample is received from a source of the fluid-borne sample 206, such as an organism or environment. In an exemplary embodiment, the source of the fluid-borne sample 206 is a human patient, but may be any type of animal having respiration. In some embodiments, the source of the fluid-borne sample is an environment such as the interior of an aerospace vehicle, the interior of a building, the interior of a car, or the like.

The fluid-borne sample is received by the input device, such as a respiration mask 202 or a ventilation system 304. In some embodiments, a flow control device 306 assists in receiving the fluid-borne sample. For example, the flow control device 306 may be a pump or humidifier for assisting the fluid-borne sample through the multi-layer filter 400. The flow control device 306 may also be a seal or vacuum device for increasing internal pressure in the input device and reducing contamination.

As the fluid-borne sample is received by the input device, at least a portion of the fluid-borne sample passes through the multi-layer filter 400. As discussed herein, the multi-layer filter 400 may comprise one or more layers including physical barrier layers 402, 404, 406, a fourth layer 408 for sample preparation, a fifth layer 410 for analyte concentration, and/or control layers comprising a first control 422.

When the fluid-borne sample is prepared such that the analyte of interest is detectable by the device, a microfluidic system 500 transports the fluid-borne sample from the multi-layer filter 400 to the analysis cartridge 600. The microfluidic system 500 may include devices for facilitating the transport of fluid, such as heaters 504, electro-osmatic pump contacts 512, and/or tubes 502 configured for capillary action. In some embodiments, the microfluidic system 500 includes an electronic device for controlling the heaters 504 and/or electro-osmatic pump contacts 512. In still further embodiments, the microfluidic system 500 includes capacitive sensors 514 or other sensors for detecting flow in the tubes 502, and allowing control over the flow rate. One or more power sources 506 may be associated with the microfluidic system 500 or the analysis cartridge 600.

The microfluidic system 500 transports the fluid-borne sample to the analysis cartridge 600, which is configured to determine the presence and/or concentration of analytes in the sample. In some embodiments, the analysis cartridge includes a temperature sensor 616, PCR chemistry 612, and/or control chemistry comprising a second control 610. In some embodiments, a computing device processor 618 controls one or more heaters 602 and/or cold finger air source 606 to control the temperature in the analysis cartridge 600. An output device 312, such as a window or display, provides an output of the result 208 of the analysis.

It should be understood that the method and mask-based device may work in concert to allow users to detect analytes of interest. The mask-based device may be configured with the features, steps, and devices discussed with respect to the method, such as the control samples, in order to assist users in detecting an analyte based on a subject's respiration.

Ventilation-Based Device for Detecting Analytes

FIG. 3 provides a diagrammatic representation of a device 300 for use in a ventilation system 304, such as a ventilation system as a component of an aerospace vehicle. The device 300 may be used to implement the method for detecting an analyte. In an embodiment, the ventilation system 304 in the aerospace vehicle 302 includes a flow control device 306, a multi-layer filter 400, a microfluidic system 500, a cartridge 600 for analysis, and an output device 312. It should be understood that any or all of the devices and features disclosed with respect to the method (FIG. 1) and/or the respiratory device (FIG. 2A) may also be implemented in the ventilation system. For example, the concentrating layer may be included in the multi-layer filter.

The flow control device may be an active or passive device. For example, an active pump or fan may be used to pass air through the ventilation system of the aerospace vehicle. In an embodiment, the fan is used to circulate air through the environments of the aerospace vehicle. As the air is circulated, the device intermittently or regularly takes a fluid-borne sample of the air to detect specific analytes. For example, the device may be configured to detect analytes of interest that are present in the environment of the aerospace vehicle. In another environment, the flow control device is a passive device, such as a non-powered ventilation system that passively takes air samples. In this embodiment, a fan or powered input device advances the fluid-borne sample through the multi-layer filter, without actively ventilating the aerospace vehicle.

The multi-layer filter may include any of the filter layers, e.g., size, charge, etc., discussed herein. Because the fluid-borne sample is passing through a ventilation system and not coming from a respiratory system of a subject, the multi-layer filter may have additional layers and/or a change in the order of layers to address the type of contaminants that may be present in a fluid-borne sample passing through a ventilation system. In an embodiment, the multi-layer filter is also replaceable. For example, the multi-layer filter may be replaced when the dissolvable filters are used for a first sample analysis.

The cartridge for analysis may be easily accessible and/or replaceable as a part of the ventilation system. In an embodiment, the cartridge is accessed by a user, pulled out, and replaced with a new cartridge either because the previous cartridge completed its analysis, the previous cartridge tested a different analyte than what the user is interested in testing, or the previous cartridge passed a predetermined time period without being used.

In an embodiment, the output device is a device that visually presents the results of the analysis to a user. In some embodiments, the output device is also configured to transmit the results of the analysis or to identify a positive result and transmit the positive result to the aerospace vehicle crew or to another party, e.g., air traffic control.

Turning now to FIG. 7, an example of a wearable collection device 200 for detecting analytes is provided. The wearable collection device 200 includes a respiration mask 202, a selectively dissolvable, multi-layer filter 400, (c) a microfluidic system 500, and (d) a cartridge 600 for sample analysis. The wearable collection device 200 may also include attachment devices 702 for securing the wearable collection device to the subject's face. In some embodiments, the attachment devices are adjustable to allow for a secure fit of the collection device to the subject's face. In this example, the wearable collection device 200 includes a transparent mask that covers the subject's eyes. It should be understood that the wearable collection device may be designed so that it covers the mouth and/or nose of the subject alone, and does not cover the eyes of the subject.

Printed Circuit Board for Microfluidic RT-PCR Analysis

In a further embodiment, the analysis chamber comprises a printed circuit board 800 ("PCB") designed to transport fluids and conduct RT-PCR analysis. In an embodiment, the PCB includes both electrical and fluidic capabilities, such as the capability to transport fluid into a chamber 802 and the capability to thermocycle the fluids in the chamber 802 via integrated heaters 804 for a RT-PCR analysis. FIG. 8 shows a PCB structure having an insulating backbone 806, such as FR4, upon which heaters 804 are formed from an electrical layer. In some embodiments, the heaters 804 comprise copper, but may include other electrically conductive material in addition to or instead of copper. A polyimide layer 808 is deposited on top of the electrical layer and used to form a fluidic chamber 802. Electrically conductive vertical structures (not shown) may also be formed within the polyimide layer 808 to provide electrical contact to the electrical layer and heaters 804.

In some embodiments, a heater 804 is integrated into the electrical layer of the PCB by using a long copper trace folded in a serpentine path as a resistor. The heater is configured to allow selective heating of the PCB, such as for implementing the thermocycle during the RT-PCR analysis. In some embodiments, the available resistances are on the order of an Ohm. For example, a half inch by half inch square resistor fabricated on a 1 oz copper (35 microns thick) layer, with a 6 mil wide trace on 6 mil spacing gives a resistance of 1.7 Ohms. This resistor allows the generation of 8.7 W of thermal power when driven at 3 amps. When the heaters 804 are separated from the chamber 802 by a polyimide layer 808, the heater 804 is thermally coupled to the chamber 802.

Optionally, the temperature profile created by the heater 804 may be smoothed by the addition of a heat smoothing layer 810 placed between the resistor and chamber. In an embodiment, the heat smoothing layer 810 comprises copper. This heat smoothing layer 810 will conduct heat from the heater 804 into the chamber 802. Those skilled in the art will understand that materials other than copper may be used for the heater 804 and/or the heat smoothing layer 810.

Temperature within the fluidic chamber may be controlled by controlling the current applied to the embedded resistor. In further embodiments, the temperature may be evaluated by determining a resistance measurement of the resistor, by using an infrared thermometer, and/or by using a thermocouple. In some embodiments, a feedback loop is generated to change and/or stabilize the temperature of the chamber 802.

In some embodiments, a transparent window into the fluidic chamber 802 is provided. The transparent window may be constructed using a polymer such as polyimide. In an embodiment, the transparent window is thin and an optical pump is able to transmit into the chamber 802. In an embodiment, the transparent window can be used to take an optical measurement of the nucleic acid concentration within the chamber 802. Displays may also be used in addition to or instead of the window as an output device for reporting activities within the fluidic chamber.

In some embodiments, the system includes external or integrated devices that allow fluorescent tags to be identified in the chamber 802. The devices may include a source 812, such as an LED or laser, which is configured to direct energy into the chamber 802. In response, the fluorescent tags emit a signal, which exits the chamber 802 and, in some embodiments, interacts with a beam splitter 814 to direct the fluorescent signal through a filter 816 and to a detector 818 (e.g., a photomultiplier, avalanche photodiode, etc.). The detector 818 is able to detect whether one or more fluorescent tags are present in the chamber 802, indicating the presence of analytes of interest and/or controls.

While the foregoing disclosure discusses illustrative embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any embodiment may be utilized with all or a portion of any other embodiment, unless stated otherwise. Still further, while a product or process may be described as comprising one or more elements or steps, it should be understood that the product or process may also consist of or consist essentially of the one or more elements or steps.

While certain exemplary embodiments have been described and shown in the accompanying drawings, it is to be understood that such embodiments are merely illustrative of and not restrictive, and that this disclosure not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the disclosure. Therefore, it is to be understood that, within the scope of the appended claims, the disclosure may be practiced other than as specifically described herein.

We claim:

1. An analyte detection device, the device comprising:
- a multilayer member configured to receive a fluid-borne sample comprising at least one analyte in combination with one or more non-analyte components, the multilayer member comprising at least:
  - a sample preparation layer comprising consecutive filter layers of a cell lysis layer and a concentrating layer, both configured to dissolve upon receiving at least a portion of the fluid-borne sample to produce a solution comprising at least a portion of the fluid-borne sample; and
  - an analysis cartridge in microfluidic communication with the multilayer member, the analysis cartridge configured to determine a presence and/or a concentration of the analyte in the solution and
- a microfluidic system providing microfluidic communication between the sample preparation layer and the analysis cartridge, the microfluidic system comprising at least one of: a capillary tube; an electro-osmatic pump contact in communication with a capillary tube; or a heater in thermal communication with a capillary tube.

2. The analyte detection device of claim 1, wherein the multilayer member further comprises at least one filter element configured to separate at least one analyte from the one or more non-analyte components prior to contact with the cell lysis layer.

3. The analyte detection device of claim 1, further comprising a concentrating layer having an affinity technique specific for the at least one analyte.

4. The analyte detection device of claim 3, wherein the affinity technique is based in whole or in part on charge-selectivity, mass-selectivity, antibody-antigen binding, bonding specificity, or a combination thereof.

5. The analyte detection device of claim 1, wherein the device comprises polymerase chain reaction chemistry.

6. The analyte detection device of claim 5, wherein at least a portion of the polymerase chain reaction chemistry is lyophilized in a dissolvable filter.

7. The analyte detection device of claim 1, further comprising a detectable marker specific to one or more of the at least one analyte.

8. The analyte detection device of claim 1, further comprising an output device configured to provide a visual indicia of the results from the analysis cartridge.

9. The analyte detection device of claim 1, wherein the device is integrated with a face mask.

10. The analyte detection device of claim 1, wherein the device is integrated with a ventilation or air-handling system of a vehicle or building.

11. A method for detection of an analyte, the method comprising:
- receiving a fluid-borne sample comprising at least one analyte in combination with one or more non-analyte components;
- introducing at least a portion of the fluid-borne sample to a sample preparation layer comprising consecutive filter layers of a cell lysis layer and a concentrating layer, both configured to dissolve upon receiving at least a portion of the fluid-borne sample to produce a solution comprising at least a portion of the fluid-borne sample;
- introducing the solution to a microfluidic system, the microfluidic system comprising at least one of: a capillary tube; an electro-osmatic pump contact in communication with a capillary tube; or a heater in thermal communication with a capillary tube;
- transporting the solution to an analysis cartridge; and
- determining a presence and/or a concentration of the at least one analyte in the sample.

12. The method of claim 11, further comprising filtering the fluid-borne sample through at least one filter to separate the at least one analyte from the one or more non-analyte components.

13. The method of claim 11, further comprising lysing a cell in the fluid-borne sample to release the at least one analyte in the solution.

14. The method of claim 13, wherein lysing is performed using at least one of chemical lysing, thermal lysing, and mechanical lysing.

15. The method of claim 11, further comprising concentrating the at least one analyte in the solution, wherein the concentrating is based at least in part on an affinity technique.

16. The method of claim 15, wherein the affinity technique is based in whole or in part on a charge-selectivity, a mass-selectivity, an antibody-antigen binding, a bonding specificity, or a combination thereof.

17. The method of claim 11, wherein the determination is performed using polymerase chain reaction.

18. The method of claim 17, further comprising providing at least a portion of the polymerase chain reaction chemistry in a lyophilized form in a dissolvable filter.

19. The method of claim 17, further comprising providing a detectable marker specific to the at least one analyte.

20. The method of claim 11, wherein the detection is performed using an Enzyme-Linked Immunosorbent Assay (ELISA), a quantitative real-time polymerase chain reaction (qPCR), or a DNA-hybridization technique.

21. The method of claim 11, wherein the introducing is performed by respiration of a user.

22. An analyte detection device, the device comprising:

a sampling device having one or more sampling ports for receiving a fluid-borne sample, the fluid-borne sample comprising at least one analyte in combination with one or more non-analyte components;

a multilayer member in fluidic communication with the one or more sampling ports, the multilayer member comprising consecutive filter layers of at least:

a filter layer configured to separate the at least one analyte from the non-analyte components in the fluid-borne sample, a cell lysis layer configured to dissolve upon receiving at least a portion of the fluid-borne sample to produce a solution comprising at least a portion of the fluid-borne sample, and a concentrating layer having an immune affinity column that binds to the at least one analyte, wherein the concentrating layer is configured to dissolve in the solution; and a real-time PCR cartridge in microfluidic communication with the multilayer member, the real-time PCR cartridge configured to determine a presence and/or a concentration of the at least one analyte in the solution.

* * * * *